United States Patent [19]

Paglione

[11] 4,292,960
[45] Oct. 6, 1981

[54] APPARATUS AND METHOD FOR APPLICATION OF RADIOACTIVE AND MICROWAVE ENERGY TO THE BODY

[75] Inventor: Robert W. Paglione, Robbinsville, N.J.

[73] Assignee: RCA Corporation, New York, N.Y.

[21] Appl. No.: 34,744

[22] Filed: Apr. 30, 1979

[51] Int. Cl.³ .............................................. A61N 5/12
[52] U.S. Cl. ..................................... 128/1.1; 128/804
[58] Field of Search ......................... 128/1.1, 653, 804

[56] References Cited

U.S. PATENT DOCUMENTS

| 2,126,257 | 8/1938 | Hird | 128/788 |
| 2,460,707 | 2/1949 | Moray | 128/1.1 |
| 3,060,924 | 10/1962 | Rush | 128/1.2 |

FOREIGN PATENT DOCUMENTS

| 342419 | 2/1931 | United Kingdom | 128/804 |
| 1045546 | 10/1966 | United Kingdom | 128/804 |
| 547985 | 12/1974 | U.S.S.R. | 128/804 |

OTHER PUBLICATIONS

"Fletcher Suit Afterloading Applicator", (Product Brochure) Radium Chemical Company, Inc., 161 East 42nd St., New York, NY.
Whalley, W. B., "RF Eradication of Tumours", Electronics & Power, May 1977, pp. 415-417.

*Primary Examiner*—Robert W. Michell
*Assistant Examiner*—Francis J. Jaworski
*Attorney, Agent, or Firm*—Samuel Cohen; Robert L. Troike

[57] ABSTRACT

Apparatus for applying radioactive and microwave energy to the walls of an internal body organ such as the uterus. An applicator having two ovoids and a tandem is positionable in the female vagina such that the ovoids are placed at the walls of the cervix and the tandem is inserted into the uterine cavity. Temperature sensing means are positioned on the periphery of the ovoids and tandem to measure the tissue environment heated by the radioactive energy and microwave energy. A controller, operating with the temperature sensing means, is provided to maintain the temperature of the tissue environment within a desired temperature range.

12 Claims, 14 Drawing Figures

APPARATUS AND METHOD FOR APPLICATION OF RADIOACTIVE AND MICROWAVE ENERGY TO THE BODY

Of interest is the following pending U.S. Patent Application, Ser. No. 023,393, entitled, "A Coaxial Applicator for Hyperthermic Treatment of the Body," filed Mar. 23, 1979 by F. Sterzer, et al.

This invention relates to an apparatus providing both radiotherapy and microwave hyperthermia for the treatment of the body. More particularly, this invention relates to an applicator positionable in the vagina and uterine cavity for emitting radioactive energy and microwave energy for the combined treatment of cancer of the cervix and uterine cavity.

It is known that curative effects of the treatment of a malignant tumor may be provided either by radiotherapy or microwave hyperthermia. Radiotherapy involves the treatment of a malignant tumor by means of x-rays or of a radioactive substances to provide curative effects. Microwave hyperthermia involves the treatment of malignant tumors by means of microwave energy to provide also curative effects. Apparatus that apply radioactive energy to the body are known. One such apparatus is described in U.S. Pat. No. 3,060,924, entitled, "APPARATUS FOR APPLICATION OF RADIOACTIVE SUBSTANCE TO PELVIC CANCER" issued Oct. 30, 1962 to Joseph C. Rush. Another is the Fletcher-Suit Applicator sold by the Radium Chemical Co. of New York, N.Y. The use of microwave energy for hyperthermia treatment of tissue is known as described in the aforementioned U.S. Patent Application, Ser. No. 020,393.

There is evidence that hyperthermia acts as a sensitizer as described in an article entitled, "Enhancement of Radiation Effects by Heating of the Tumor" by A. Yerushalmi and I. Har-Kadar, published in Israel J. of Med. Sci. Vol. 10, pp. 772-776, 1974. When combinations of the two treatment methods are applied to the body, a much reduced radiation dose is necessary to produce lethal damage to the tumor. Correspondingly, a decrease in the radiation dosage reduces the detrimental accumulative effects of radiation exposure to the patient. There remains a need in the medical art for an apparatus that provides both radioactive energy and microwave energy for the combined radiotherapy and microwave hyperthermia treatment of body tissues or tumors.

An apparatus and method are provided according to this invention for radiotherapy and microwave hyperthermia treatment of the anterior portion (cervix) and the posterior cavity (uterine cavity) of a body cavity. The apparatus comprises means for providing radioactive energy and microwave energy to selected portions of the body cavity. The radioactive energy is provided by a radioactive substance disposed in one portion of a container while the microwave energy is provided by a radiating element disposed in another portion of the same container.

Figure 1:
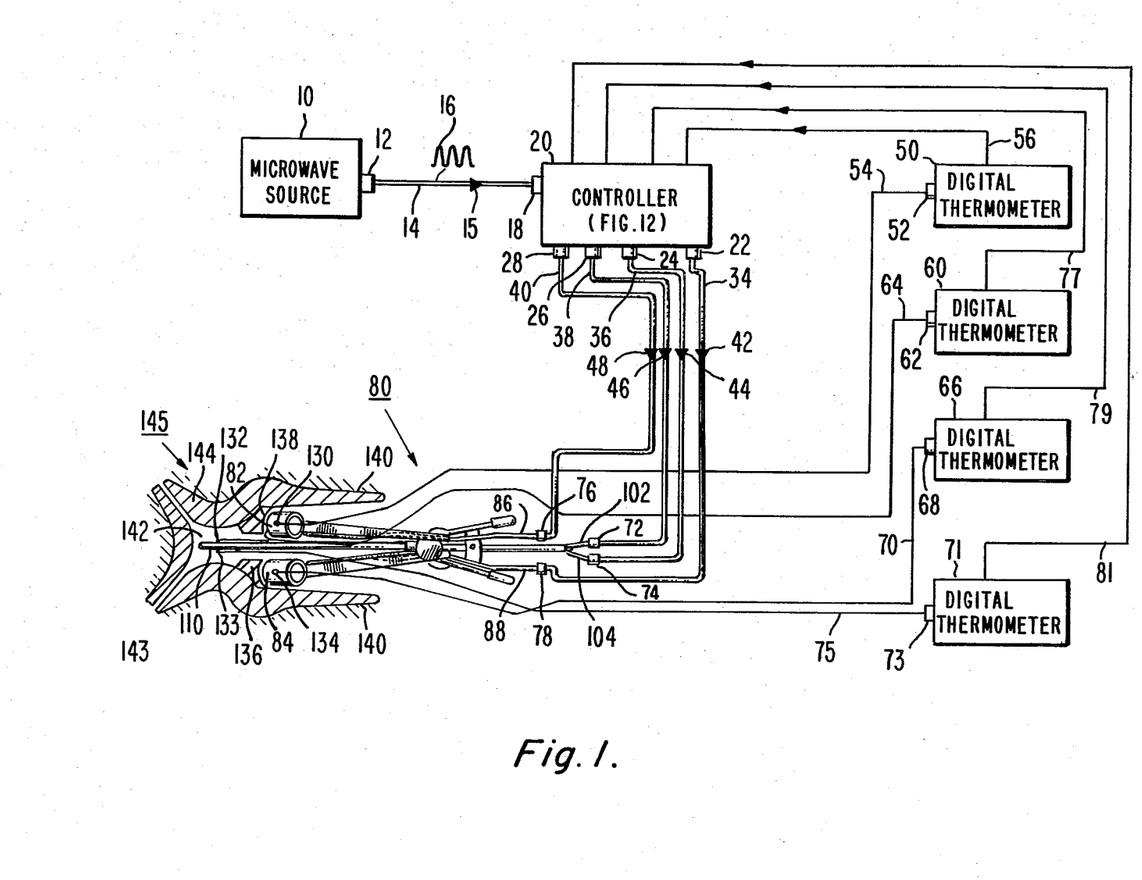
FIG. 1 is a block schematic of a system using an appparatus of one embodiment of the invention.

The internal portions and relative positions of the human female body shown in FIG. 1 such as the uterus 145, the vagina 140, the walls of the cervix 136 and 138, the uterine cavity 142, and the endometrium 144 and the myometrium 143 are for illustrative purposes only. For descriptive information of the female body see any text on anatomy. See, for example, Gray's Anatomy by Henry Gray, 1977, Bounty Books, New York.

The female generative organs include the ovaries (not shown), the Fallopian Tubes (not shown), the uterus 145 with its cervix (shown in FIG. 1 as cervical walls 136 and 138) and the vagina 140. The accessibility of the uterus 145 for medical examination is typically by way of the vagina 140. The invention to be described, uses the accessibility to the uterus 145 via the vagina 140, for positioning an applicator 80 to emit both radioactive energy and microwave energy, for the combined radiotherapy and microwave hyperthermia treatment of the cervical walls 136 and 138 and the uterine cavity 142.

Radiotherapy, as known in the art, is a means for treating certain types of malignant tumors of the human being. Radiotherapy generally comprises the use of ionizing radiation such as x-rays and radioactive substances. According to the present invention, radiotherapy shall mean the use of only radioactive substances for the radiotherapy and shall not mean the use of x-rays. As understood in the art, radioactive substances such as radioactive Cesium-137 and other metallic substances provide a spontaneous emanation of energy in the form of gamma rays. For further information, reference is made to Textbook of Radiotherapy by Fletcher and Lea, Febiger Publishing Co., Philadelphia, 1975, for a more detailed explanation of the use of radiotherapy for the treatment of malignant tumors.

Applicator 80 (as shown in detail in FIG. 2) comprises ovoids 82 and 84 and a tandem 110 for emitting radioactive energy and microwave energy. The so-called "ovoids" and "tandem" are structures well-known in the radiotherapy art. Ovoids 82 and 84 are each positionable at diametrically opposite cervical walls 138 and 136, respectively. Ovoids 82 and 84, to be described hereinafter in detail, have a cylindrical shape and a wall thickness that provides proper spacing of a radiation source, disposed within ovoids 82 and 84, from the cervical walls 138 and 136, respectively, to be radiated. Ovoids 82 and 84 are formed of a suitable low-loss plastic dielectric material, such as teflon, to allow a microwave signal 16 launched from a radiator 158 positioned within each ovoid 82 and 84, to pass through the walls of the ovoids 82 and 84 to irradiate and heat the cervical walls 138 and 136, respectively. Tandem 110 (shown in detail in FIG. 5 to be described hereinafter in detail) is centrally positioned on the applicator 80 and is formed of an elongated rod with a width suitable for positioning in the uterine cavity 142. Tandem 110 has positioned within it a radioactive substance that emits radioactive energy into the uterine cavity 142. Tandem 110 is formed of a suitable low-loss plastic dielectric material, such as teflon, which is transparent to microwave signals 16.

Applicator 80 emits radioactive energy and electromagnetic energy. The microwave signal 16 is coupled from source 10 in the direction of arrow 15, via coaxial connector 12, coaxial cable 14 and coaxial connector 18 to controller 20. Controller 20 couples the microwave signal 16, in response to d.c. temperature control voltages via signal paths 56, 77, 79 and 81, as will be explained hereinafter, in respective transmission lines 34, 36, 38 and 40 in the direction of arrows 42, 44, 46 and 48, respectively, to applicator 80. Coaxial lines 34, 36, 38 and 40 are provided with coaxial connector 22 and a coaxial cable 34, a coaxial connector 24 and a coaxial cable 36, a coaxial connector 26 and a coaxial cable 38, and a coaxial connector 28 and a coaxial cable 40, respectively. Controller 20 by means of a conventional power splitter 216, shown in FIG. 12, divides the microwave signal 16 equally among coaxial cables 34, 36, 38 and 40. Cables 34, 36, 38 and 40 are suitably attached to applicator 80 via microwave connectors 78, 74, 72 and 76 respectively. Microwave connectors 72, 74, 76 and 78 are of conventional type suitable for coaxial cables 102, 104, 86 and 88 respectively. Connector 76 is suitably attached to a coaxial cable 86 which terminates in ovoid 82. Microwave connector 78 is suitably attached to coaxial cable 88 which terminates in ovoid 84. Microwave connectors 72 and 74 are suitably attached to coaxial cables 102 and 104, respectively, which are internal to tandem 110.

The means for measuring the heat within the environment irradiated by the microwave signal 16 is provided by temperature sensing means, such as thermocouples 130, 134, 132 and 133 suitably attached to ovoids 82, 84 and tandem 110 respectively. Thermocouples 130, 132, 133 and 134 are connected to digital thermometers 50, 60, 66 and 71 via signal paths 54, 64, 70 and 75 respectively. Signal paths 54, 64, 70 and 75 are connected to digital thermometers 50, 60, 66 and 71 via connectors 52, 62, 68 and 73. Digital thermometer 50 (and also 60, 66 and 71) is suitably a Model No. BAT-8 manufactured by the Bailey Instrument Co. of Saddle Brook, N.J.

Figure 2:
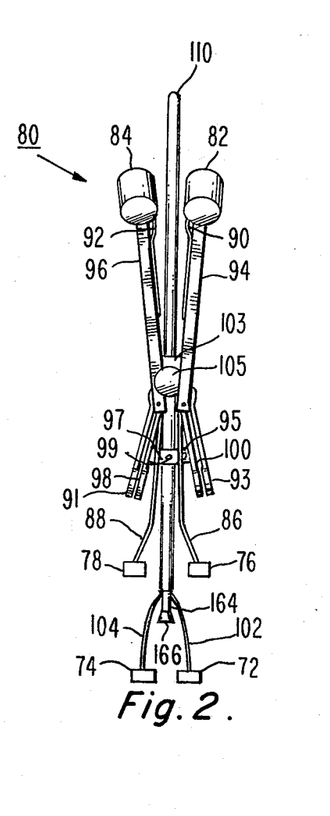
FIG. 2 illustrates the applicator.
Figures 3A, 3B, 3C:
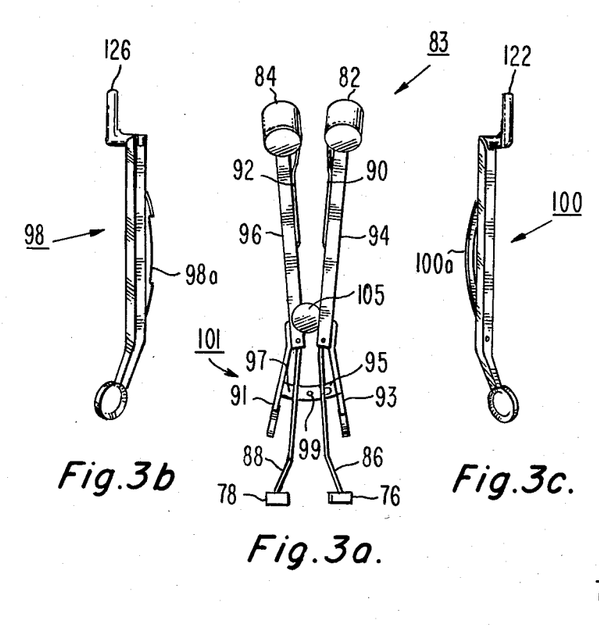
FIGS. 3a, 3b, 3c and 4 illustrate the various parts of the applicator.

Reference is now made to FIG. 2 showing applicator 80 in more detail. Ovoids 82 and 84 are connected to the upper end of a right and left armhousing 94 and 96, respectively. Housings 94 and 96 are herein termed "colpostats," a term well-known in this art. Colpostat 96, having typically a length of approximately 10.8 cm, is rigidly attached by suitable brazing to member 91, having typically a length of approximately 5.7 cm. Similarly, colpostat 94 also having a length of approximately 10.8 cm is rigidly attached by suitable brazing to member 93 having a length also approximately 5.7 cm. A member 95 having a central aperture is suitably rigidly affixed to member 93. A member 97 having an opening to receive a screw 99, not shown, is rigidly affixed to member 91. A nearly circular member 105 is suitable rigidly affixed to colpostat 94. Colpostat 96 is recessably adapted to receive member 105. Member 105 allows colpostats 94 and 96 to be positionally spaced from each other in divergent directions. Screw 99 screwed through a threaded opening in member 97 is positioned into the aperture of member 95 and tightened to mate together member 95 and 97 and thus establish a fixed position. The combination of positional members 91, 93, 95 and 97 and screw 99 (shown in FIG. 3a) will hereinafter be referred to as "adjustable means" 101. Adjustable means 101 is adjustable such that ovoids 82 and 84 are placed in a position abutting each other called the "insertion" position and further adjustable to positions where the ovoids 82 and 84 are divergently disposed from each other into positions called the "spread-apart" positions. The insertion position of ovoids 82 and 84 is used for inserting applicator 80 into the vagina 140. Conversely, the "spread-apart" positions of ovoids 82 and 84 provide various adjustable positions used to abut the ovoids 82 and 84 against the diametrically opposite cervical walls 138 and 136. Colpostat housings 94 and 96 have a hollow rectangular shaft in which solid members 100 and 98, more clearly shown in FIGS. 3c and 3b respectively, are respectively inserted. Solid members 98 and 100 have spring-loaded members 98a and 100a, respectively, to hold the solid members within the hollow shafts of colpostats 96 and 94. Solid members 98 and 100 have at one end hollow buckets 126 and 122, respectively, suitably composed of a metal such as brass. Buckets 122 and 126 are loaded with the Cesium radiation source which is typically in the shape of a pellet, for example, Cesium-137 pellets manufactured by 3 M Nuclear Products Div., St. Paul, Minn.

Applicator 80 shown in its assembled form in FIG. 2 is comprised of solid members 98 and 100, main housing 83 of applicator 80 and tandem 110 shown in FIGS. 3b, 3c, 3a and 4 respectively. Coaxial cable 86 is routed through a tubing 90 into ovoid 82. Tubing 90 is located external from the colpostat housing 94 on the side facing tandem 110. The internal portion of tube 90 is along the lower left inner wall (not shown) of the colpostat 94 and the spring loaded member 100a is indented such as not to contact the inner portion of tube 90. Colpostat 94 is provided with a suitable opening through the lower left wall to allow exit of the tube 90. Tube 90 continues along the outside lower left portion of colpostat 94 and gradually bends upward to the outside upper left portion of colpostat 94, at which point tube 90 enters ovoid 82. Cable 88 is routed through tubing 92 and into ovoid 84 in a similar manner as described for cable 86. Coaxial cables 86 and 88 are of the type RG-178B/U supplied by Belden Corp., Richmond, Ind., as their model #83265.

Figure 4:
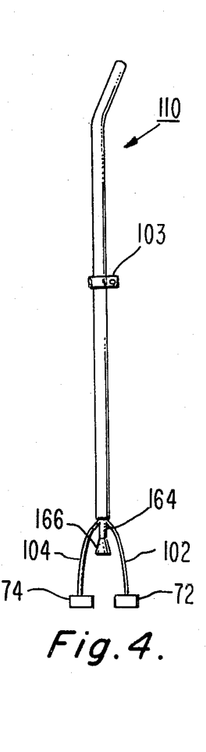
Figure 5:
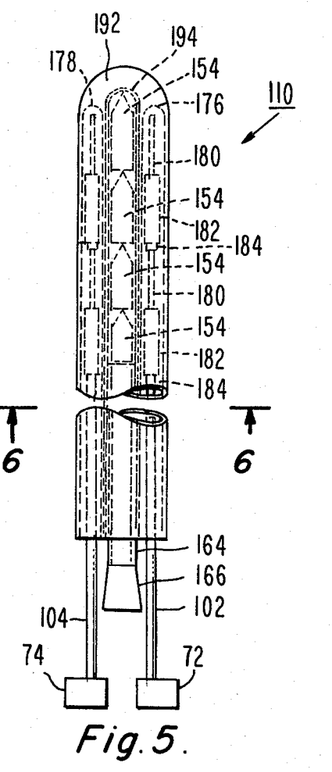
FIG. 5 shows the details of the tandem (110) of the applicator.

Tandem 110, shown in FIG. 4, is positioned under the main housing 83 and into the uterine cavity 142 shown in FIG. 1. An adjustable clamp 103 is positioned on tandem 110 to abut against the nearly circular member 105, shown in FIG. 2, to thereby prevent the tandem from being forced out of the uterine cavity 142. Reference is now made to FIG. 5 which shows tandem 110 in greater detail.

Tandem 110 has a typical longitudinal length of 25.4 cm. Tandem 110 has a hollow shaft 194 having a typical diameter of 2.41 mm and a typical length of 25.4 cm. A pellet tube 164 having a typical outer diameter of 2.28 mm, a typical inner diameter of 1.78 mm and typical length of 25.4 cm is loaded with Cesium-137 pellets 154 and inserted into hollow shaft 194. Pellet tube 164 is preferably formed of a high-impact polystyrene material. The number of Cesium-137 pellets 154 loaded into pellet tube 164 is determined by the desired radioactive dosage required for the uterine cavity 142 under treatment. FIG. 5 shows four (4) pellets 154 loaded into pellet tube 164 and inserted into hollow shaft 194. Pellets 154 are maintained in position by a pellet holder 166. Pellet holder 166 is preferably formed of a high-impact polystyrene material. Pellet holder 166 has a typical diameter of 1.59 mm. The diameter of pellet holder 166 positioned at the entrance to pellet tube 164 is tapered to a 2.11 mm diameter that when pellet holder 166 is inserted into pellet tube 164 it mates and forces against pellet tube 164 such that pellet holder 166 becomes wedged into pellet tube 164. The fixed position of pellet holder 166 internal within pellet tube 164 maintains the location of the inserted pellets 154 at the upper portion of pellet tube 164.

Figure 6:
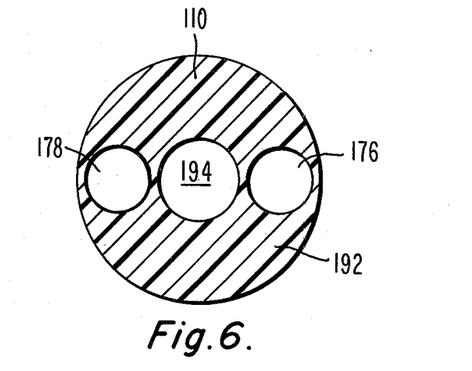
FIG. 6 shows a cross-section of the tandem as seen along section lines 6—6 of FIG. 5.
Figure 7:
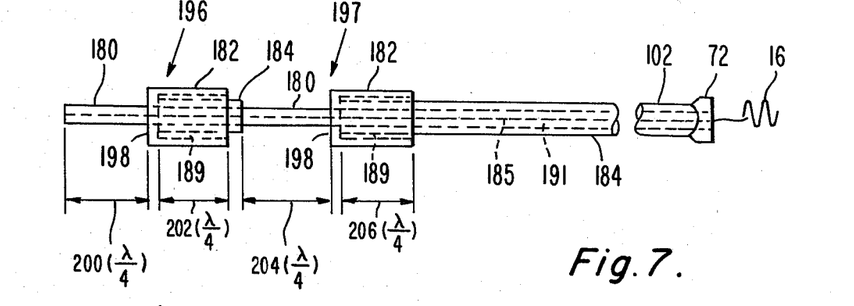
FIG. 7 illustrates the chokes and the unshielded ends which together serve as the microwave radiator within the tandem shown in FIG. 5.

Tandem 110 has two additional hollow shafts 176 and 178 having a typical diameter of 1.59 mm. A cross-section of tandem 110, as seen along section lines 6—6 of FIG. 5, showing all three (3) hollow shafts 178, 194 and 176 is shown in FIG. 6. Referring back to FIG. 5, coaxial cables 102 and 104 are respectively inserted into hollow shafts 176 and 178. Coaxial cables 102 and 104 are of the type UT-34 supplied by Uniform Tubes Inc., Collegeville, Pa. Coaxial cables 102 and 104 are substantially identical and therefore only cable 102 will be described in detail. Coaxial cable 102 has unshielded ends 180 and chokes 182 positioned at the end of the cable that is inserted into shaft 176. FIG. 5 shows coaxial cable 102 having two unshielded ends 180 and two chokes 182. A pair consisting of unshielded end 180 and choke 182 substantially span the longitudinal distance of two cesium pellets 154. For the four pellets 154 shown inserted in pellet tube 164 in FIG. 5 it is preferred to have two pairs of unshielded end 180 and choke 182, such that a microwave signal 16 launched from coaxial cable 102 radiates substantially the same longitudinal portion as the radioactive energy emitted from the four Cesium-137 pellets 154. If a tumor located in the uterine cavity 142 only requires the radiation dosage provided by either one or two radioactive pellets 154, the one or two radioactive pellets 154 along with suitably positioned dummy pellets, if needed, may be inserted into the pellet tube 164 and arranged such that the radioactive pellets are aligned to the tumor to be treated. For this one or two pellet 154 treatment, a single unshielded end 180 and choke 182 is positioned opposite the radioactive pellets. Reference is now made to FIG. 7 showing cable 102 in greater detail.

Coaxial cable 102 has an inner conductor 185 and an outer conductor 184 formed of a semi-rigid conductive material such as copper with an outer diameter having a typical value of 0.89 mm. Choke 182 is a suitable hollow metallic sleeve, having a typical inner diameter of 1.06 mm for positioning about outer conductor 184. Choke 182 and the outer conductor 184 are rigidly joined by a solder junction 198. The outer conductor 184 of coaxial cable 102 is insulated from choke 182, except at junction 198, by a dielectric material 189 such as teflon, to prevent choke 182 from contacting outer conductor 184 except at noninsulated junction 198. Unshielded ends 180 and chokes 182 combine to form half-wave dipole antennas 196 and 197 having junctions 198 as their feed-points for launching microwave signal 16.

The number of half-wave dipole antennas 196 and 197 determines the number of junctions 198, that is, two dipole antennas 196 and 197 provide two junctions 198. As shown in FIG. 7, coaxial cable 102 has two junctions 198 thus providing dipole antennas 196 and 197. Unshielded ends 180 extend from junction 198 away from connector 72 at a first and second location shown as distances 200 and 204 respectively. Conversely, chokes 182 extend from junction 198 towards connector 72 at a first and second location shown as distances 202 and 206 respectively.

Distances 200, 202, 204 and 206 are equal to $\lambda_g/4$ where $\lambda_g$ is defined by the following equation:

$$\lambda_g = f \frac{c}{\sqrt{\epsilon}} \quad (1)$$

where c is the speed of light in vacuum ($3.0 \times 10^8$ meters/sec), f is the microwave frequency in cycles per second, and $\epsilon$ is the dielectric constant of the media 191 and 189, such as teflon, between the inner conductor 185 and outer conductor 184 and the outer conductor 184 and the choke 182 respectively. Using equation (1) for a typical value of 2.45 GHz, distances 200, 202, 204 and 206 are equal to 2.11 cm. The characteristic impedance ($Z_o$) of coaxial cable 102 may be represented by the following formula:

$$Z_o = \frac{138}{\sqrt{\epsilon}} \times \log_{10}\left(\frac{b}{a}\right) \quad (2)$$

where $\epsilon$ is the dielectric constant of the medium 191 and "a" and "b" are respectively the center conductor diameter and the inner diameter of the outer conductor. For a characteristic impedance of 50 ohms, $$\frac{1}{\sqrt{\epsilon}}$$

is 0.69 for teflon and "a" equals 0.2 mm and "b" equals 0.69 mm.

Figures 8, 10:
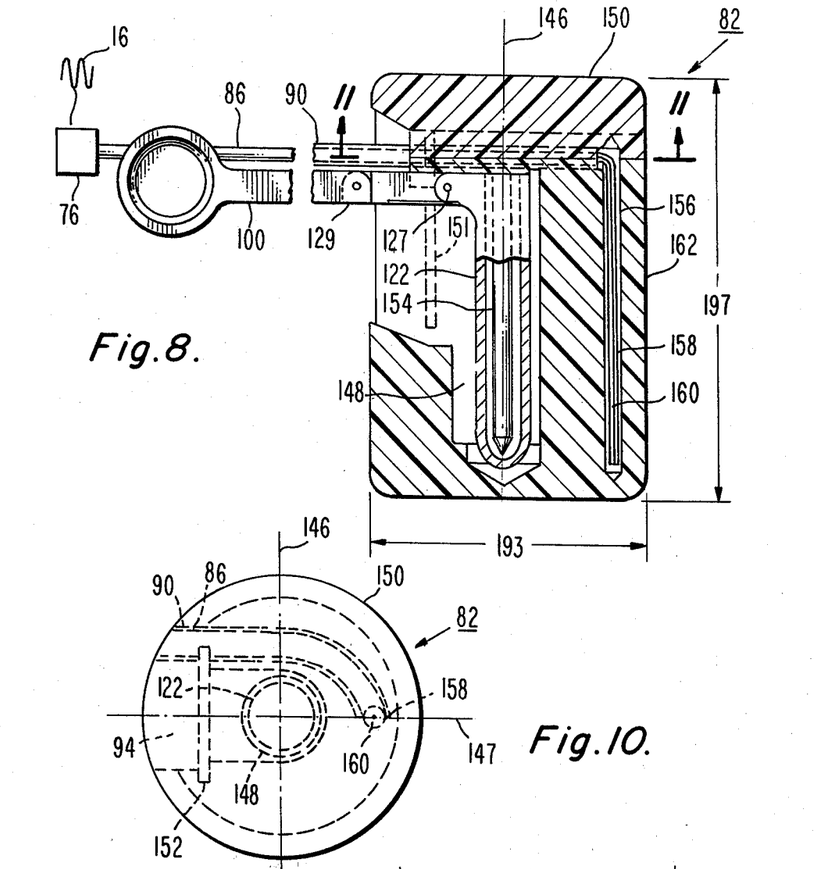
FIG. 8 shows a cross-section of the ovoid (82).
FIG. 10 is a top view of the top portion of the ovoid (82).
Figure 9:
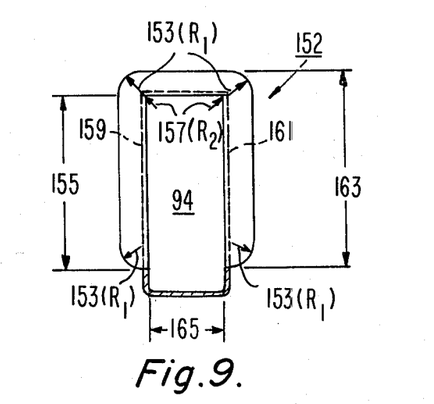
FIG. 9 illustrates the details of the colpostat flange (152).

Reference is now made to FIG. 8 showing ovoid 82 in detail. Ovoids 82 and 84 are substantially identical and thus only ovoid 82 need be described in detail. Ovoid 82 has a diameter 193, typically 1.9 cm, and a height 197 typically 4.4 cm. Ovoid 82 has a top portion 150 and a bottom portion 162 each suitably provided with a portion of a hollow groove 151. Hollow 151 allows the top portion 150 and bottom portion 162 to be mated with a flange 152. Reference is now made to FIG. 9 showing flange 152 in detail.

Flange 152 is preferably formed of a nonoxidizing material such as stainless steel. Flange 152 has typical dimensions of an inner width 165 of 6.35 mm and a height 155 of 12.5 mm. The outer distance 163 of flange 152 is typically 14 mm. Flange 152 has a radius 153 ($R_1$) at the four corners, as shown in FIG. 9, typically 1.58 mm. Flange 152 has a further radius 157 ($R_2$) typically 0.794 mm where it abuts colpostat 94 as shown in FIG. 9. Colpostat 94 is suitably rigidly affixed to flange 152 extending along locations 159 and 161. The mating of the top portion 150 and bottom portion 162 to flange 152 via hollow 151 attaches ovoid 82 to colpostat 94. Conversely, to detach ovoid 82 from colpostat 94, top portion 150 is separated from bottom portion 162 and bottom portion 162 is then separated from colpostat 94. The provision for easily removing void 82 from colpostat 94 allows for convenient replacement of ovoid 82 when desired.

Referring back to FIG. 8, bottom portion 162 has two hollow shafts 148 and 156 for insertion of brass bucket 122 and coaxial cable 86, respectively. Brass bucket 122 attached to member 100 is positioned through the internal portion of colpostat housing 94, previously discussed, and forced against the shaft 148. The force of bucket 122 against shaft 148 causes the brass bucket to pivot about hinged points 127 and 129 of member 100 and thereby snap into a vertical position, shown in FIG. 8, in which the center of Cesium-137 pellet 154, inserted in bucket 122, is approximately aligned to a center line 146 of ovoid 82.

Cable 86 is routed through tube 90 into shaft 156. The end of coaxial cable 86 within shaft 156 has an unshielded end 158 having as its inner conductor 160. The unshielded end 158 has a length of 2.11 cm which equals one-quarter wavelength at the operating frequency in accordance with equation (1). End 158 is a monopole antenna for launching microwave signal 16 coupled to cable 86.

Figure 11:
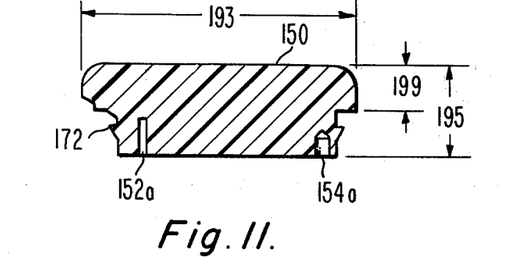
FIG. 11 is a cross-section of the top portion of the ovoid (82) as seen along section line 11—11 of FIG. 10.

Top portion 150 of ovoid 82 is shown in detail in FIGS. 10 and 11. Portion 150 shown in FIG. 10, has positioned within it a portion of the previously described tube 90 through which coaxial cable 86 is inserted. End 158 within shaft 156 is approximately aligned to the horizontal center line 147 of ovoid 82. Portion 150, shown in FIG. 11, as seen along section lines 11—11 of FIG. 8, has a diameter 193 previously described and an overall height 195 having a typical value of 6.35 mm. The segment of top portion 150 not insertable into bottom portion 162 is shown as 199 and has a typical height of 3.12 mm. Lip 172, shown in FIG. 11, attaches the top portion 150 of ovoid 82 to the bottom portion 162 of ovoid 82.

Figure 12:
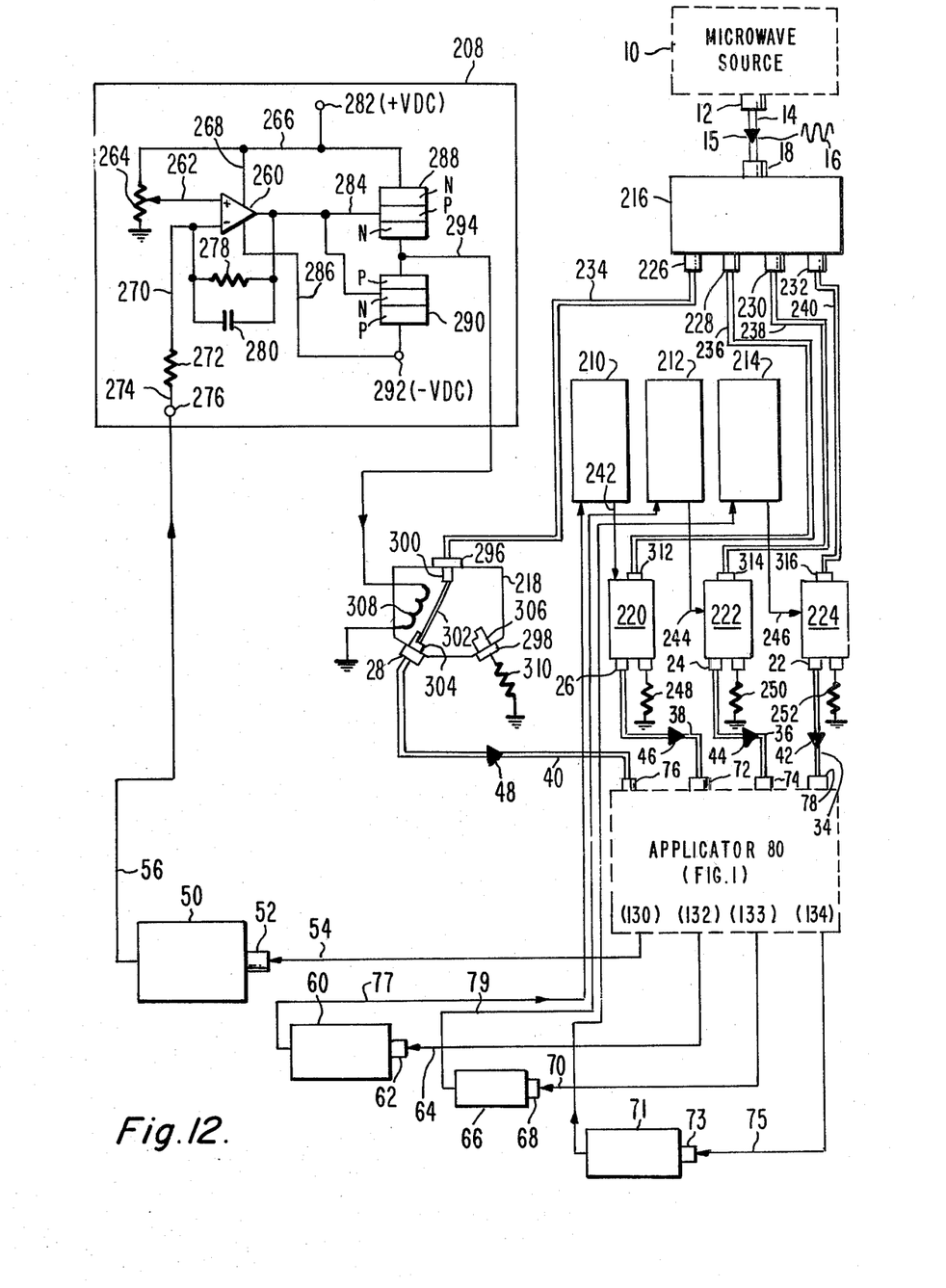
FIG. 12 is an electrical schematic of the controller (20) of FIG. 1.

Reference is now made to FIG. 12 showing controller 20 in detail for coupling signal 16 to ovoids 82 and 84 and tandem 110. It should be understood that the details and description thereof to be given for control circuit 208 is also applicable to control circuits 210, 212 and 214 not shown in detail, operating with digital thermometers 60, 66 and 71 respectively. It should be further understood that the detailed description to be given for coaxial switch 218 operating with control circuit 208 is also applicable to coaxial switches 220, 222 and 224 operating with control circuits 210, 212 and 214 respectively. To better understand the detailed operation of coaxial switch 218 and control circuit 208 the overall flow of microwave signal 16 from microwave source 10 to applicator 80 will be given.

Microwave signal 16 from source 10 is routed to a conventional power divider 216 of controller 20. Divider 216 splits the power of microwave signal 16 equally among four output ports 226, 228, 230 and 232. Output ports 226, 228, 230 and 232 are respectively routed to coaxial switches 218, 220, 222 and 224. Coaxial switches 218, 220, 222 and 224 are connected to ports 226, 228, 230 and 232 via coaxial cable 234 and connector 296, coaxial cable 236 and connector 312, coaxial cable 238 and connector 314, and coaxial cable 240 and connector 316 respectively. Coaxial switches 218, 220, 222 and 224 selectively controlled by circuits 208, 210, 212 and 214, respectively, as will be explained hereinafter, couple microwave signal 16 to applicator 80. Dummy loads 310, 248, 250 and 252 connected to coaxial switches 218, 220, 222 and 224, respectively, provided a proper termination of microwave signal 16 when coaxial switches 218, 220, 222 and 224, as will be explained, decouple microwave signal 16 from applicator 80.

Coaxial switch 218 is suitably a Hewlett-Packard switch part No. 8761A. Switch 218 includes an input coaxial connector 296 and two output coaxial connectors 28 and 298, and a flexible reed contact 302 that is magnetically coupled to a winding 308. Each coaxial connectors 296, 28 and 298 have inner conductors 300, 304, and 306, respectively. Reed contact 302 is connected at one end to inner conductor 300 of input connector 296, while the other end thereof is positionable in response to signals passing through the winding 308 to be electrically connected with the inner conductor 304 or 306. the polarity of the voltage applied to winding 308 determines the position of reed contact 302. A positive voltage applied to winding 308 positions reed contact 302 to inner conductor 304 of coaxial connector 28 and thus connects microwave signal 16 to applicator 80. A negative voltage applied to winding 308 positions the reed contact 302 to the inner conductor 306 and thus connects microwave signal 16 to dummy load 310. The application of a positive or negative energizing signal to winding 308 is controlled by a differential amplifier 260 of control circuit 208 operating with transistors 288 and 290. Differential amplifier 260 is suitably a type RCA CA741 operational amplifier. Transistor 288 is a NPN type and transistor 290 is a PNP type.

Differential amplifier 260 has two inputs, one a non-inverting input on signal path 262 and the other an inverting input on signal path 270. The input on path 262 is preset to a d.c. value indicative of a predetermined temperature e.g., 43° C., that is to be maintained during the treatment of the cervical walls 136 and 138 and uterine cavity 142. The preset value is set by adjusting potentiometer 264. The potentiometer 264 is connected between a voltage source at terminal 282, having a particular polarity such as a positive d.c. voltage, and a reference voltage such as ground, such that the preset value is adjustable therebetween. The input voltage to differential amplifier 260 on path 270 is suitably a d.c. voltage proportional to temperature measured by digital thermometer 50 which is coupled to controller 20 via signal path 56, terminal 276, signal path 274, and resistor 272. The d.c. voltage is indicative of the temperature of a treated tissue as measured by thermocouple 130 located at the cervical wall 138. Differential amplifier 260 is connected to positive voltage (+VDC) at terminal 282 and negative voltage (−VDC) at terminal 292 via paths 268 and 286, respectively. Differential amplifier 260 produces an output voltage on path 284 proportional to the differential voltage existing between paths 262 and 270. When the voltage on path 270 is less than the preset value at input 262, differential amplifier 260 produces a positive voltage on path 284, rendering transistor 288 conductive. Transistor 288 being conductive provides a positive voltage to winding 308 of coaxial switch 218 via path 294 thereby providing the path for connecting microwave signal 16 to connector 76 of applicator 80. When the voltage on path 270 exceeds the preset value at input 262, a negative voltage is generated on path 284, turning off transistor 288 and allowing transistor 290 to be conductive. Transistor 290 being conductive provides a negative voltage to winding 308 of coaxial switch 218 thereby decoupling microwave signal 16 from connector 76 and further connecting the microwave signal 16 to the dummy load 310. A resistor 278 and a capacitor 280 connected between the inverting input path 270 and the output path 284 of amplifier 260 provide a feedback network the determines the response time and the gain of differential amplifier 260 to the differential signal between paths 262 and 270.

In operation, when the temperature of the cervical wall 138, as measured by thermocouple 130, is below the preset value established by potentiometer 264 the microwave signal 16 is coupled via switch 218 to connector 76 for irradiation of the cervical wall 138. The irradiation by signal 16 continues until the temperature of the cervical wall 138 exceeds the preset value. The operation is repeated as switch 218 couples and decouples signal 16 from the connector 76 in response to the temperature of the cervical wall 138 as sensed by thermocouple 130.

Control circuits 210, 212 and 214 operate with digital thermometer 60, 66 and 71, respectively, in a similar manner as described for control circuit 208 operating with digital thermometer 50. Digital thermometers 60, 66 and 71 supply a d.c. signal to their respective control circuits 210, 212 and 214 proportional to the temperature measured by thermocouple 132, 133 and 134. If the temperature of tissue at uterine cavity 142 or cervical wall 136 as measured by thermocouples 132 and 133, and 134, respectively, exceeds a preset value established by control circuits 210, 212 or 214, coaxial switch 220, 222 or 224 selectively decouple microwave signal 16 from their respective connectors 72, 74 and 78 of applicator 80. It should now be appreciated that circuits 208, 210, 212 and 214 provide separate controls to couple and decouple microwave signal 16 to cervical walls 138 and 136 and uterine cavity 142 in response to the temperatures measured by thermocouples 130, 134, 132, and 133 respectively. It should be further appreciated, that while the preferred embodiment provides means to measure the temperature at the interface of the applicator 80 and the tissue 136, 138 and 142 being treated, the temperature does not have to be controlled during the treatment. Thus, for example, past performance data can be used to couple microwave signal 16 to the applicator 80 for a predetermined time period at a power level predetermined from such data to effectively generate the heat required without direct temperature control.

Reference is now made to FIG. 1 to describe the placement of thermocouples 130, 134, 132 and 133 on ovoids 82 and 84 and tandem 110, respectively. Thermocouple 130 is positioned and suitably affixed to the periphery of ovoid 82 in contact with cervical wall 138 and in alignment with internally positioned coaxial cable 86 prior to the insertion of applicator 80 into vagina 140. Thermocouple 134 is positioned and suitably affixed to the periphery of ovoid 84 in contact with cervical wall 136 and in alignment with internally positioned coaxial cable 88 prior to the insertion of applicator 80 into vagina 140. Similarly, thermocouples 132 and 133 are positioned on the periphery of tandem 110 at the diameter line bisecting the hollow shafts 178, 194 and 176 of tandem 110 such that one is in alignment with one of the two previously described junctions 198 of coaxial cable 102 and the other is in alignment with the corresponding junction 198 of coaxial cable 104, prior to insertion of tandem 110 into uterine cavity 142. If desired, two additional thermocouples, similar to thermocouple 132 and 133, may be further positioned on tandem 110 to provide a total of four thermocouples each aligned with one of the four junctions 198 provided by coaxial cables 102 and 104. The total of four thermocouples as compared to two thermocouples 132 and 133 provides a more accurate measurement of heat distribution along the tandem 110. It should be appreciated that each additional thermocouple should be provided with an additional digital thermometer (similar to 50), control circuit (similar to 208) and microwave switch (similar to 218) in order to obtain the added accuracy in temperature measurement and control.

After the thermocouples 130, 134, and 132 and 133 are affixed to the periphery of ovoids 82, 84 and tandem 110, respectively, a suitable expandable rubber material, such as a latex finger cot, may be placed over each ovoid 82 and 84 and tandem 110 to thus prevent the substances of the human body from directly contacting the ovoids 82 and 84 and tandem 110 and further to prevent any irritation by thermocouples 130, 132, 133 and 134 when applicator 80 is inserted into the female organ.

Applicator 80, having the solid member 98 and 100 removed, is adjusted by means of adjustable means 101 of applicator 80 to its "insertion" position.

The insertion position of ovoids 82 and 84 allows applicator 80, with tandem 110 positioned under adjustable means 101, to be inserted into vagina 140. The applicator 80, after insertion, is now adjusted, by means of adjustable means 101 to a "spread-apart" position such that ovoids 82 and 84 are divergently positioned from each other and abut the diametrically opposite cervical walls 138 and 136. Tandem 110 located under adjustable means 101 is thus positioned into uterine cavity 142. The positioning of the ovoids 82 and 84 at cervical walls 138 and 136, respectively, and tandem 110 in the uterine cavity 142 may be verified by an imaging device. Upon verification of the correct positioning of ovoids 82 and 84 and tandem 110, the microwave cables 40, 38, 36 and 34 may be respectively connected to the applicator 80 via connectors 76, 72, 74 and 78. However, microwave source 10 is not yet energized. The radioactive substance 154 is subsequently inserted into ovoids 82 and 84 and tandem 110 via brass buckets 122 and 126 and pellet tube 164 respectively. Insertion of the radioactive source into ovoids 82 and 84 and tandem 110 initiates the radiotherapy portion of the treatment of the cancerous lesions of the cervical walls 136 and 138 and the uterine cavity 142. It is well known that the radiotherapy, described herein as the emission of gamma rays from a radioactive substance 154, given alone in appropriate doses (rads and schedules (time duration per day), may provide curative effects in the treatment of certain malignant tumors. Applicator 80, having the radioactive substance 154 disposed within ovoids 82 and 84 and tandem 110, provides an apparatus that may be used only for radiotherapy treatment of the cervical walls 136 and 138 and uterine cavity 142 when the microwave signal 16 is inactivated. The ovoids 82 and 84 and tandem 110 emit gamma rays from the radioactive substance 154 in an omnidirectional pattern for the radiation of the cervical walls 136 and 138 and uterine cavity 142. If desired, a suitable type of metal shielding such as lead may be partially positioned around the hollow shaft compartments within the ovoids 82 and 84 and tandem 110 holding the radioactive substance 154 to provide a directional pattern for the radiation being emitted from radioactive source 154.

Once the ovoids 82 and 84 and tandem 110 are properly positioned, loaded with the radioactive substance 154 and connected to an energized microwave source 10, the combined radiotherapy and microwave hyperthermia treatment of cervical walls 136 and 138 and uterine cavity 142 is initiated.

The conjunctive use of radiotherapy and microwave hyperthermia has been the subject of wide discussion. The reasons for conjunctive radiotherapy and hyperthermia treatment is related to the following factors:

1. Heat generated by microwave energy effectively destroys radio-resistant hypoxic tumor cells and decreases the oxygen enhancement ratio (OER). Such a destruction is described in an article entitled *"Hyperthermia and the Oxygen Enhancement Ratio"* by Y. E. Robinson in the Proceedings of the International Symposium of Cancer Therapy by Hyperthermia and Radiation, Washington 1975, pp. 66-74.

2. Heat-induced vasodilation caused by hyperthermia treatment results in a better oxygen supply to the tumor and, therefore, in a higher fraction of oxygenated radiosensitive cells.

3. Cell heating interferes with the repair of radiation-induced sublethal damage. Such an interference is described by K. Overgaard and Y. Overgaard in an article entitled *"Pathology of Heat Damage Studies on the Histopathology in Tumor Tissue Exposed In Vivo to Hyperthermia and Combined Hyperthermia and Roentgen Irradiation"* published in Proceedings of the International Symposium of Cancer Therapy of Hyperthermia and Radiation, Washington 1975, pp. 115-127.

4. Cells in the S-phase of the cell cycle, most resistant to radiation, are effectively destroyed by heat developed by the hyperthermia treatment. Such a destruction is described in an article by A. Westra and W. C. Dewey entitled *"Variation in Sensitivity to Heat Shock During the Cell Cycle of Chinese Hamster Cells in Vitro,"* published in the Int J. Radiation Biology, Vol. 19, pp. 467-477, 1971.

5. Hyperthermia is a sensitizer to radiation. Hyperthermia acting as a sensitizer is described in an article by A. Yerushalmi and I. Har-Kadar entitled *"Enhancement of Radiation Effects by Heating of the Tumor"* published in Israel J. of Med. Sci., Vol. 10, pp. 772-776, 1974.

Conjunctive use of radiotherapy and hyperthermia reduces the total radiation dosage necessary to produce lethal damage to the tumor. Radiotherapy treatment of cancer of the uterus has a typical treatment time of 72 hours. The radiotherapy in conjunction with hyperthermia is expected to reduce the total treatment time of cancer of the uterus by a factor of one-third or more. The microwave source 10, that provides the microwave energy for the hyperthermia treatment, supplies signal 16 at a predetermined frequency and intensity. The microwave signal 16 provides substantial uniform heating of specific volumes of tissue and controller 20 regulates the amount of heating during the treatment periods. A microwave frequency of 2.45 GHz for signal 16 provides a penetration depth of 1.7 cm for the type of tissue being treated such as the cervical wall 136. Microwave signal 16 radiated from the radiators disposed within ovoids 82 and 84 and tandem 110 provides preferential heating of the walls of the cervix 138 and 136 and the uterine cavity 142, respectively. The preferential heating of the cervical walls 136 and 138 and the uterine cavity 142 occurs in close proximity to the microwave radiators. This occurs because the radiators are located near the outside walls within the ovoids 82 and 84 and tandem 110. The microwave signal 16 launched from the radiators internal to the ovoids 82 and 84 and tandem 110 travels a minimum distance for penetration of the cervical walls 138 and 136 and uterine cavity 142. The power density of the launched signal 16 decreases approximately by the square of the distance traveled from the radiating probes. Thus, the maximum intensity of signal 16 penetrates the cervical walls 136 and 138 and uterine cavity 142 in close proximity to the radiators. Conversely, the power density of signal 16 penetrating the remaining environment of the uterus 145 is less intense. The heat developed by the microwave signal 16 is directly proportional to the intensity of signal 16. Thus, the cervical walls 136 and 138 and uterine cavity 142 in close proximity to the radiators are preferentially heated. The microwave radiation heats and thus elevates the temperature of the cervical walls 136 and 138 and the uterine cavity 142 to the preferred hyperthermic range of 42°-43° C.

As previously discussed, controller 20 operates to selectively decouple the microwave signal 16 from cervical wall 136, cervical wall 138 or uterine cavity 142 if either the temperature of the cervical wall 136, cervical wall 138, or uterine cavity 142 equals or exceeds a preset value. A typical preset value of 42.5° C. for each of the tissues 136, 138 and 142 is selectively established via control circuits 208, 210, 212 and 214. If either the temperature of the cervical walls 136 and 138 or uterine cavity 142 does not equal or exceed the 42.5° C. preset value, microwave energy continues selective irradiation of tissues 136, 138 and 142.

It should now be appreciated that the practice of this invention provides an apparatus which applies, via the vagina, microwave energy and radioactive energy for treatment of cancerous lesions within the cervical walls 136 and 138, and the uterine cavity 142.

What is claimed:

1. An apparatus for use with a radioactive substance for applying radioactive and microwave energy to the walls of a body cavity comprising:
   a source of microwave signals having a predetermined amplitude and frequency,
   means including a radiator responsive to said microwave signals for radiating said signals,
   means for coupling said microwave signals to said radiating means,
   a container having a first compartment adapted for receiving a quantity of said radioactive substance and having in a second compartment thereof said radiator, and
   means for supporting said container in said body cavity.

2. The apparatus according to claim 1 wherein the body cavity is the uterus of a female human being including the cervix and uterine cavity, and said radiating means includes a plurality of radiators, and including a second container having a first compartment adapted for receiving a quantity of said radioactive substance and having in a second compartment thereof one of said radiators, and wherein said container support means includes means for supporting said first-mentioned container and said second container on opposing walls of said cervix.

3. The apparatus according to claim 2 including a third container having a first compartment adapted for receiving a quantity of said radioactive substance and in a separate compartment thereof one of said radiators, and wherein said container support means further includes means for supporting said third container in said uterine cavity.

4. The apparatus according to claim 3 wherein said support means comprises two hollow arms, one end of each of said two arms being respectively connected to a pivotal means and the other respective end of each arm being connected to said first and second containers, said pivotal means being pivotable to position each of said first and second containers at opposite walls of said cervix and further comprising means to limit the movement of said third container support means to a predetermined distance within said uterine cavity, said two hollow arms including means for loading said first and second containers with said radioactive substance and carrying said microwave coupling means.

5. The apparatus according to claim 3 wherein said radiator in said third container includes a plurality of radiating elements, and wherein said third container comprises a cylinder of a low-loss dielectric material, said cylinder having three tubular compartments extending longitudinally of said cylinder with a first tubular compartment thereof adapted for receiving a predetermined quantity of said radioactive substance, and having in a second and a third tubular compartment thereof said radiators; and a means for inserting into and removing from said first compartment of said third container said predetermined quantity of said radioactive substance while the apparatus is in situ with said cavity.

6. The apparatus according to claim 5 wherein said microwave coupling means comprises a coaxial cable, and further wherein said radiators include radiating elements, said radiating elements within said second and third tubular compartments having a length equal to an integer multiple of one-half wavelength of said microwave signals, said radiating elements formed from unshielded portions of said coaxial cable, each of said unshielded portions having a length equal to one-quarter wavelength of said microwave signals.

7. Apparatus according to claim 5 further comprising temperature measuring means comprising a temperature sensor attached to one of said containers to provide electrical signals indicative of the temperature of said cavity.

8. Apparatus according to claim 7 wherein each of said containers includes a temperature sensor, and said temperature measuring means further comprises control means responsive to said electrical signals of each of said sensors for controlling said microwave signals to each of said radiators to maintain the temperature of the associated tissue surrounding said cavity at a predetermined temperature.

9. Apparatus according to claim 8 wherein said control means comprises:

means for generating electrical signals indicative of predetermined reference temperatures, means responsive to said electrical signals indicative of said predetermined reference temperatures and said electrical signals indicative of the temperatures of said walls of said cervix adjacent to each of said first and second containers and said electrical signals indicative of the temperature of said uterine cavity for generating output signals when each of said predetermined reference temperatures exceeds said temperatures indicative of said cavity portions, means responsive to said output signals to selectively couple said microwave signals to each of said radiators, and means responsive to the absence of said output signals to selectively decouple said microwave signals from each of said radiators.

10. The apparatus according to claim 2 wherein said radiators include radiating elements, said radiating elements within said first and second containers having a length equal to an integer multiple of one-quarter wavelength of said microwave signals.

11. The apparatus according to claim 1 wherein said container is formed of a low-loss dielectric plastic material.

12. A method for applying radioactive and microwave energy to the walls of the uterus of a female human being comprising the steps of:

a. providing radioactive energy at predetermined radiation dosages to the walls of said uterus by introducing a source of radioactive energy within said uterus; and b. irradiating the walls of said uterus with microwave signals having predetermined amplitude and frequency by introducing a radiator of said microwave signals within said uterus.

* * * * *